United States Patent [19]
Auerbach et al.

[11] Patent Number: 4,927,766
[45] Date of Patent: May 22, 1990

[54] GAS CONSTITUENT MEASUREMENT AND RECORDING

[75] Inventors: Abraham Auerbach, Monsey, N.Y.; Sonia Friedman, Lawtenceville, N.J.

[73] Assignee: The BOC Group, Inc., Murray Hill, New Providence, N.J.

[21] Appl. No.: 866,810

[22] Filed: May 27, 1986

[51] Int. Cl.⁵ ............... G01N 31/22; G01N 35/00
[52] U.S. Cl. .................................. 436/44; 356/445;
422/66; 422/83; 422/86; 422/91; 436/126; 436/155; 436/164
[58] Field of Search ............... 73/23; 356/405, 445, 356/36; 374/163; 422/55, 78, 66, 83, 86-88, 91; 436/5, 6, 44, 155, 164, 126

[56] References Cited
U.S. PATENT DOCUMENTS

| | | | |
|---|---|---|---|
| 3,558,280 | 1/1971 | Panson et al. | 422/90 |
| 3,961,248 | 1/1976 | Kawamura | 422/97 |
| 4,042,329 | 8/1977 | Hochstrasser | 436/169 X |
| 4,049,383 | 9/1977 | Burton et al. | |
| 4,105,919 | 8/1978 | Bridges et al. | |
| 4,115,067 | 9/1978 | Lyshkow | 422/86 X |
| 4,257,777 | 3/1981 | Dymond et al. | |
| 4,350,660 | 9/1982 | Robinson et al. | 422/90 |
| 4,352,016 | 9/1982 | Duffy et al. | |
| 4,379,402 | 4/1983 | Harman, III | |
| 4,446,719 | 5/1984 | Lambert | |
| 4,459,043 | 7/1984 | Luke | 356/43 X |
| 4,495,793 | 1/1985 | Hager | |
| 4,551,425 | 11/1985 | Zemel | 422/90 |
| 4,636,088 | 1/1987 | Rosencwaig et al. | 356/445 X |
| 4,668,635 | 5/1987 | Forster | 436/134 |

OTHER PUBLICATIONS
Levinson et al.; Changes in the Reflectivity of Metal Films as a Result of Heating with Short Laser Radiation Pulses; Sov. J. Quant. Electron., vol. 4, No. 5, Nov., 1974, pp. 680–682.

Primary Examiner—Michael S. Marcus
Attorney, Agent, or Firm—Larry R. Cassett; Roger M. Rathbun

[57] ABSTRACT

The molecular concentration of a constituent such as oxygen of an anesthetic agent in a gas is measured by contacting the gas with the surface of a solid body, momentarily heating the surface so that the constituent reacts at the surface to alter a property of the surface such as reflectivity, and determining the degree or rate of alteration occasioned by the heating step. The momentary heating operation may be performed by light from a laser focused on to a small localized region. The body surface can include a thin film of a material such as a metal reactive with the gas constituent of interest at elevated temperatures. The preferred methods provide extraordinarily rapid response, and also form a permanent record of each measurement. Where the gas is at substantially constant pressure, the measured molecular concentration can be interpreted as an indication of the proportion of the constituent in the gas. Where the gas is of known composition, the molecular concentration can be interpreted as a measurement of the total gas pressure. Similar techniques are be applied to identify an unknown constituent in a gas or to detect presence of an incorrect constituent, such as an incorrect anesthetic agent in an anesthesia system. Apparatus and recording media are also disclosed.

55 Claims, 3 Drawing Sheets

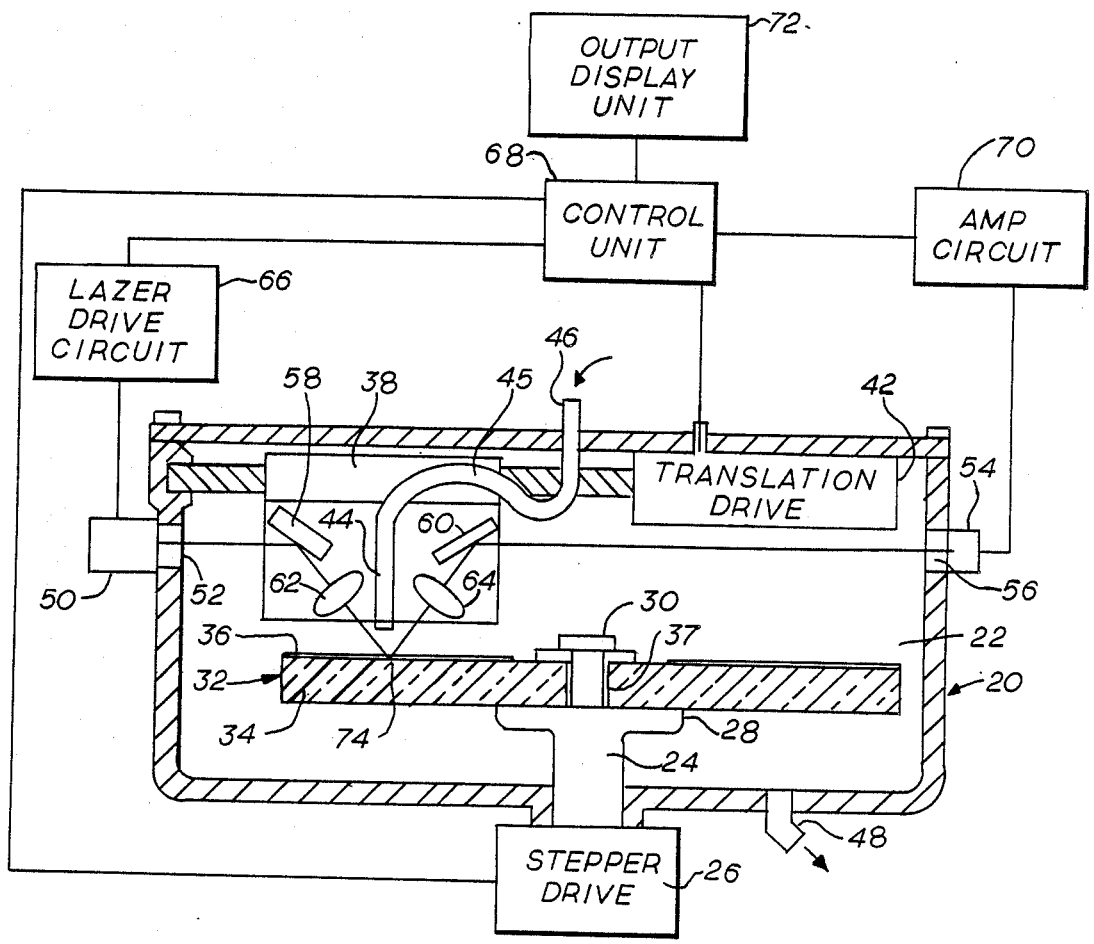
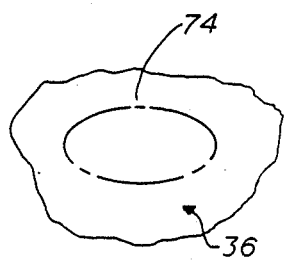
FIG. 2
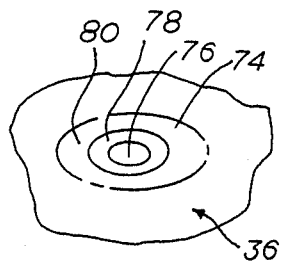
FIG. 3
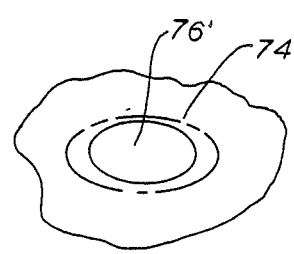
FIG. 4

GAS CONSTITUENT MEASUREMENT AND RECORDING

BACKGROUND OF THE INVENTION

The present invention relates to processes and apparatus for measuring the molecular concentration of a constituent in a gas.

The need to determine the proportion of a particular gaseous constituent in a gas arises in various industrial, scientific and medical operations. For example, it is often necessary to determine the proportion of oxygen and/or anesthetic agent in the gas supplied to a surgical patient.

Various means for measuring the proportion of a particular constituent in a gas have been proposed heretofore. As set forth in U.S. Pat. Nos. 4,257,777 and 4,049,383, the amount of light produced by a chemiluminescent reaction involving the constituent of interest is measured and the proportion of the constituent is determined from the measured amount of light. The concentration of a particular gas constituent may also be measured by monitoring the changes in conductivity of a semiconductor resulting from the absorption of the constituent on the semiconductor surface, as disclosed in U.S. Pat. No. 4,495,793. Spectrophotometric measurements, thermal conductivity measurements, and the like have also been employed for measuring the concentration of a particular constituent.

Many of the prior methods and apparatus respond slowly, and hence cannot provide accurate measurements during rapid changes in gas composition. The prior methods and apparatus typically require careful technique and delicate or expensive instrumentation. Moreover, the methods and apparatus utilized heretofore typically have provided only a transitory output signal representative of the concentration of the constituent of interest. Thus, to obtain a permanent record of the concentration, it has been necessary to record the output signal utilizing additional equipment such as electronic recording apparatus. Such apparatus adds complexity and cost and can also introduce error in the recorded readings.

SUMMARY OF THE INVENTION

One aspect of the present invention provides a method for measuring the molecular concentration of a constituent in a gas. The term "molecular concentration" means the number of molecules per unit volume. As the molecular concentration of any constituent in a gas varies directly with the proportion of that constituent in the gas and directly with the total absolute pressure of the gas, measurement methods according to the present invention may be utilized to determine either the (1) proportion of the particular constituent or (2) the total absolute pressure of the gas. Typically, the total absolute pressure of the gas is known or constant, and the measured molecular concentration provides a direct measure of the proportion of the constituent in the gas.

In a measurement method according to this aspect of the present invention, the gas is contacted with a surface of a solid body and such surface is momentarily heated so that the gas reacts at the surface. The reaction alters a property of the surface, typically an optical property such as reflectivity. The degree or rate of alteration in the surface property is related directly to the molecular concentration of the constituent at the surface during the momentary heating. Accordingly, the molecular concentration is determined simply by determining the degree or rate of alteration of the surface property.

Preferably, the surface is momentarily heated by directing a pulse of heating radiant energy, such as light from a laser, onto a localized region of the surface so that the reaction occurs at such localized region. The degree of alteration in the surface property is determined for the localized, heated region. Where the property altered in the reaction is an optical property such as reflectivity, it can be measured by directing measurement radiant energy onto the localized region and measuring the amount of such radiant energy reflected by the localized region. Most preferably, a plurality of localized regions are heated in temporal sequence, as by sequential pulses of the heating radiant energy. The degree of alteration in the property of each localized region is measured separately so as to provide a series of measurements of the molecular concentration, each such measurement indicating the molecular concentration at the time of the heating step for one localized region.

Preferably, the change in the surface property incident to the reaction of the gas is permanent. Thus, the degree of alteration in the surface property may be determined either concomitantly with the heating operation or thereafter. The degree of alteration in the surface property may be determined either by comparing a value of the surface property measured after heating with a known standard value of that property before heating, or by measuring the surface property both before and after heating and comparing the two measured values of such surface property. In a particularly preferred embodiment of the present invention, adapted to provide a series of "real time" molecular concentration values, the reflectivity of each region is measured immediately before and immediately after that region is heated. Where the alteration in the surface property affected by the reaction is permanent, the permanently altered surface provides a permanent record of the molecular concentration. The permanent record can be read back at any time merely by measuring the altered surface property and comparing the value of such property with a known standard value for the property before heating.

The reaction which occurs upon heating includes the gas constituent of interest and preferably also includes a material in the body surface, either as a reactant or as a catalyst. The material of the surface may be selected to react only with the particular gas constituent of interest. In measuring the molecular concentration of oxygen, the surface may include one or more metals selected from the group consisting of tin, silver, nickel and copper. The surface may also include antimony or indium together with the other metals. Thus, combinations of tin and indium or, preferably, tin and antimony may be employed. The metals may be present at the surface, before reaction in the form of free metal. The surface, prior to reaction may also include minor amounts of nitrides or oxides of the metals. The nitrides and oxides promote absorption by the surface of the radiant energy used in the heating step. Oxidation of surfaces containing the aforementioned metals decreases their reflectivity. The decrease in reflectivity is directly proportional to the molecular concentration of oxygen at the surface during the heating step. Moreover, the change in reflectivity upon oxidation is permanent.

For measurement or recordation of the concentration of organic gas constituents such as halogenated compounds the surface may include one or more group VIII metals such as, e.g., palladium or ruthenium, or may include aluminum. These surfaces may include oxides or nitrides of the metals. It is believed that upon heating in contact with a halogenated organic compound, the group VIII metals or aluminum either catalyze the decomposition of the organic compound or else reduce the organic compound. Regardless of the actual mechanism of reaction, the compound reacts to form a dark, apparently carbonaceous solid product which deposits on the surface, thereby permanently reducing the reflectivity of the surface. The degree of change in reflectivity depends on the molecular concentration of the halogenated compound.

Methods according to this aspect of the present invention are particularly useful in measuring or recording the molecular concentrations of the most common anesthetic agents, such as enflurane, halothane and isoflurane, and may also be employed with common halogenated hydrocarbon refrigerants.

With the preferred radiant energy heating methods, the heating step may be completed in less than about 500 milliseconds, preferably less than about 250 milliseconds, and most preferably less than about 10 milliseconds. Accordingly, the heating step can be repeated rapidly to provide repeated measurements of the molecular concentration at closely spaced intervals, and hence to provide accurate recordation and measurement of rapidly fluctuating molecular concentrations. Each localized region may be very small, so that a body of reasonable surface area can be used for a large number of molecular concentration determinations and can serve as a compact permanent record of many molecular concentration values. Moreover, the preferred, small localized regions can be heated rapidly by radiant energy at relatively low power levels, such as those provided by simple and economical diode lasers. Further to facilitate rapid heating with reasonable power levels, the body preferably includes only a thin, reactive, typically metal-containing film, on a substantially heat insulating substrate typically formed from a nonmetallic material such as glass.

For a given gas constituent, the extent of reaction and the degree of alteration in the surface property depend upon the temperature attained during the heating step, and hence depend upon the energy of the heating radiant energy pulses, i.e., on the power level and duration of the heating pulses. Typically, a heating pulse of a given energy level will yield useful measurements within a given useful range of molecular concentrations. Increasing the heating pulse energy shifts the useful range downwardly, and hence permits measurements of lower molecular concentration valves, whereas decreasing the heating pulse energy tends to provide the reverse effect. In a particularly preferred method according to the present invention, the heating pulse energy on each measurement cycle may be controlled in response to the results obtained on one or more preceding cycles.

Different gas constituents, having different reactivities, require different temperatures, and hence different heating pulse energies, to provide the desired reaction. A further aspect of the present invention utilizes this effect to discriminate between gas constituents. This aspect of the present invention thus provides methods for identifying an unknown constituent in a gas as one of plural known possible constituents of differing reactivities. For example, an unknown anesthetic agent which could possibly be halothane, enflurane or isoflurane can be identified. In preferred identification methods according to this aspect of the invention, the gas containing the unknown constituent is contacted with the surface of the solid body and the body surface is momentarily heated to a known extent, as by applying a heating radiant energy pulse of known energy content. The degree of alteration, if any, in a surface property such as reflectivity caused by reaction of the unknown constituent at the surface is measured to provide information as to the relationship between the extent of heating and the degree of alteration in the surface property for the gas containing the unknown constituent. That information is compared with the corresponding information for gasses containing the various known possible constituents.

Different localized regions of the surface can be heated to different extents as by radiant energy pulses of different energy levels, while in contact with the gas containing the unknown constituent, so that in at least one region, the surface property is altered to a predetermined degree. The pulse energy or extent of heating required to produce that predetermined degree of alteration can be compared with the pulse energy required to produce the corresponding degree of alteration with gasses containing the known possible constituents. Conversely, a single region may be heated to a predetermined extent and the resulting degree of alteration, if any, in reflectivity or other surface property can be compared to the degree of alteration expected with at least one gas containing the known possible constituent.

The identification provided by methods according to the present invention may be a "positive identification," i.e., a determination of what the unknown constituent is, or may be a "negative identification," i.e., a determination that the unknown constituent is not a particular possible constituent. Such negative identification can be employed to detect incorrect filling of an anesthesia system, as by determining that the anesthetic agent present in an anesthetic gas mixture is not the agent which should be present.

As will be appreciated, the relationship between extent of heating and degree of alteration in the surface property for each constituent will vary with the molecular concentration of the constituent. However, for many practical systems, the differences in this relationship among different constituents are for greater than any differences which might be caused by variations in molecular concentration. Thus, the identification method can accurately identify the unknown constituent even where the molecular concentration of the unknown constituent in the gas cannot be accurately known in advance. Once the unknown constituent has been positively identified, its molecular concentration can be determined by measurement methods in accordance with the present invention, using heating pulses of the appropriate energy for the constituent as identified.

The present invention also provides apparatus for recording and/or measuring the molecular concentration of a constituent in a gas. The recording apparatus preferably includes means for retaining a body, means for contacting the gas with a surface of the body and means for momentarily heating the surface so that a property of the surface is altered by reaction of the gas at the surface. The measurement apparatus preferably includes all of these components, and also includes means for determining the degree or rate of alteration of the surface property caused by the reaction of the gas, as by measuring said surface property after the heating step. The determining means may also be operative to measure the surface property before the surface is heated, and to compare the measured values before and after heating.

Preferably, the heating means includes means for directing a series of heating radiant energy pulses to a series of localized regions of the body surface in temporal sequence. The heating means may include a laser for providing the heating radiant energy. The determining means may also include means for providing measurement radiant energy and directing the measurement radiant energy onto the surface, and means for detecting radiant energy reflected from or transmitted through the surface upon application of the measurement radiant energy. The measurement radiant energy generating means may include a laser. Preferably, the same laser is incorporated in both the heating means and the measurement means. Control means may be provided for operating the laser in a relatively high power mode to provide the heating radiant energy and in a relatively low power mode to provide the measurement radiant energy.

Many of the components utilized in the apparatus can be similar to those employed in so-called "compact disc" digital sound recording playback equipment. Thus, the apparatus may consist of simple, readily available, components and can be simple, rugged and economical.

Yet another aspect of the present invention provides a body or recording medium which may be used with the aforementioned processes and apparatus. The medium preferably has an exposed surface including a material which is reactive with the gas constituent of interest at a first, elevated temperature but substantially nonreactive with such constituent at a second, lower temperature. Preferably, the material of the exposed surface on the recording medium is substantially nonreactive with the gas constituent at ambient or room temperature. The medium preferably includes a substrate of limited thermal diffusivity, preferably less than about $10^{-2}$ cm$^2$/sec, and a thin reactive film on the substrate at its exposed surface, the film preferably being less than about 2,000 Angstroms thick. Preferably, the film is substantially reflective to measurement radiant energy and is adapted to become substantially nonreflective upon reaction of the gas constituent of interest. The film may incorporate a dopant to facilitate absorption of heating radiant energy. Thus, the film may include the reactive metals referred to above. Moreover, the medium may include two different films of differing compositions occupying different areas of the body surface as, for example, a tin-containing film on one area for oxygen measurement or recordation and an aluminum film on another area for enflurane measurement or recordation. The recording medium may be in the form of a small disc, similar in size and shape to those employed as so-called "compact disc" digital sound records. Desirably, the recording medium includes means for engaging the body-retaining features of a gas constituent measurement and/or recording instrument so as to link the body to the instrument for use.

According to still further aspects of the present invention, the reactions employed in the gas constituent measurement and recordation methods described above can be employed for other purposes. Thus, digitally-encoded information can be recorded by contacting a gas with a surface and applying pulses of radiant energy to localized regions of the surface in a pattern corresponding to the information. The reaction of the gas at the surface caused by heating alters the surface and hence marks the surface in a pattern corresponding to the digital information. As small localized regions can be marked by the reaction, substantial amounts of information can be stored in small surface areas.

Other objects, features and advantages of the present invention will be apparent from the detailed description of the preferred embodiments set forth below, taken in conjunction with the accompanying drawings.

BRIEF DESCRIPTION OF THE DRAWINGS

FIG. 1 is a schematic, partially sectional view of apparatus according to one embodiment of the invention;

FIGS. 2 through 4 are schematic views, on an enlarged scale of a portion of the apparatus illustrated in FIG. 1 during different stages of a method according to the present invention;

DETAILED DESCRIPTION OF THE PREFERRED EMBODIMENTS

Figure 5:
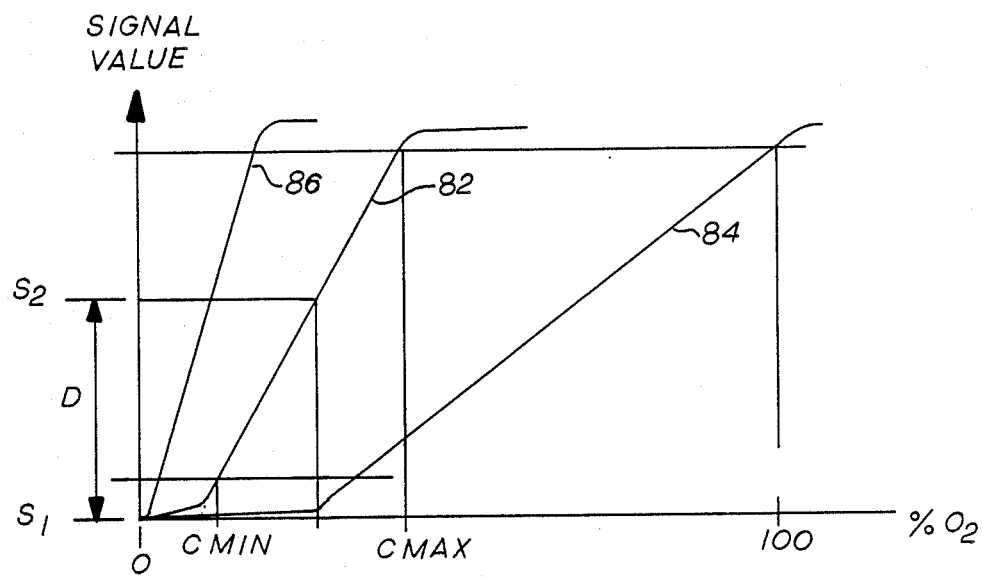
FIGS. 5, 6 and 7 are graphs showing families of output curves for the apparatus of FIG. 1.

The apparatus illustrated in FIG. 1 includes a housing 20 defining an enclosed chamber 22. A shaft 24 is rotatably mounted to the housing and connected to a stepper drive 26. The upper end of the shaft is provided with a flange 28 and a bolt 30 for retaining a flat, disklike body or recording medium 32. Body 32 includes a glass substrate 34 and a thin film 36 on the upper surface of the substrate. The film consists essentially of copper with a minor amount of copper nitride; its thickness is greatly exaggerated in FIG. 1 for clarity of illustration. Body 32 also has a hole 37 extending through it at its central axis for receiving and engaging bolt 30.

A carriage 38 is slideably mounted to the housing 20 above body 32 for movement radially with respect to the axis of shaft 24. Carriage 38 is linked to a translation drive unit 42. Thus, carriage 38 can be aligned with any portion of film 36 by rotation of shaft 24 and hence of body 32 under the influence of stepper drive 26 and by radial movement of the carriage under the influence of translation drive 42. A nozzle 44 is mounted to carriage 38 and directed downwardly towards film 36. Nozzle 44 is connected via a flexible hose 45 to a gas inlet port 46. A gas outlet port 48 is connected to the interior of chamber 22, below body 32.

A diode laser 50 is mounted to housing 20 and aligned with a transparent window 52 in the housing. A photodetector 54 is mounted to the opposite side of housing 20 and is aligned with a further transparent window 56 in the wall of the housing. Mirrors 58 and 60 and lenses 62 and 64 are mounted to carriage 38 for focusing light from laser 50 into a small active zone disposed beneath nozzle 44 and for focusing light reflected from the active zone onto photodetector 54.

The laser is powered by laser drive circuit 66, which in turn is linked to control unit 68. Laser drive circuit 66 is arranged to actuate laser 50 so as to provide either a measurement pulse of light at a preselected low power level or a heating pulse having any one of several preselected combinations of pulse power and pulse duration, as commanded by control unit 68.

Photodetector 54 is connected to signal processing and amplification circuit 70, which is arranged to transmit to control unit 68 a signal inversely proportional to the amount of light impinging upon photodetector 54. Control unit 68 is connected to output display unit 72. Control unit 68 is also linked to stepper drive 26 and translation drive 42.

In a process according to one embodiment of the present invention, a gas containing an unknown proportion of oxygen is supplied to the apparatus via gas inlet port 46. The gas passes into chamber 22 via nozzle 44 and out of the chamber via outlet port 48. The gas pressure at inlet port 46 is controlled so that gas passing from nozzle 44 and contacting film 36 is under a substantially constant, known absolute pressure.

Control unit 68 initially commands translation drive 42 and stepper drive 26 to remain stopped and hence to hold carriage 38 and body 32 stationary. Laser 50 produces a low power measurement pulse, the light in the measurement pulse being directed via window 52 and mirror 58 to lens 62, which focuses the light into the active zone. The light impinges on the localized region 74 of film 36, which is disposed in the active zone of the apparatus, and hence at the focal point of lens 62. The size and shape of localized region 74 illuminated by the light from the laser, as indicated by broken lines in FIG. 2, are determined by the cross section of the light beam incident on film 36, and hence by the characteristics of the laser and the optical elements utilized to direct and focus the incident light.

The light in the measuring pulse is reflected from region 74 and passes via lens 64, mirror 60 and window 56 to photodetector 54. The quantity of light impinging on the photodetector varies directly with the reflectivity of the film 36 in region 74. In response to the light reflected during this first measurement pulse, signal processing and amplification circuit 70 generates a first signal $S_1$ having a value inversely proportional to the amount of light impinging upon the photodetector 54 and hence inversely proportional to the reflectivity of film 36 in region 74. As the film, at this stage of the process, has a high reflectivity, the value of signal $S_1$ is low. This value is stored by control unit 68. The energy of the measuring pulse is too low to cause any appreciable heating of the film.

After the first measuring pulse, control unit 68 commands laser drive circuit 66 and hence laser 50 to emit a heating pulse having a preselected power level and duration according to one set of predetermined values stored in control unit 68. The heating pulse, like the first measuring pulse, passes via window 52 and mirror 58 to lens 62, and is focused in the same active zone as the first measuring pulse. Accordingly, the heating pulse illuminates the same localized region 74 of the film as initially illuminated by the first measuring pulse. Despite the initially high reflectivity of the film, some of the light in the heating pulse is absorbed, and hence converted to heat, by the film in region 74. Some of the heat so generated is conducted out of the film by the underlying substrate 34 and out of localized region 74 by the adjacent regions of film 36. However, these effects are limited by the relatively low thermal diffusivity of the substrate and by the limited thermal conductivity of the thin film. Thus, the heating pulse momentarily heats the film in region 74. Typically, the film at the center of region 74 reaches a somewhat higher temperature than the film at the margins of the region because of conduction losses from the margins and because the incident light typically has the greatest intensity at the center of the illuminated region.

As the temperature of the film in region 74 rises, the copper in the film begins to react with the oxygen in the gas. This reaction converts the free metallic copper in the film to copper oxide. As copper oxide is substantially transparent, the film within region 74 is transformed from a reflective, free metal film to a transparent, and hence nonreflective copper oxide film. The extent of this transformation depends upon the temperature attained by the film during the heating pulse and upon the molecular concentration of oxygen in the gas in contact with the film. Because the temperature attained by the film typically is highest adjacent the center of region 74, the extent of transformation typically is greatest adjacent the center of region 74, and becomes progressively less towards the margins of such region. For a heating pulse of typical power level and duration, and for a typical concentration for oxygen in the gas, the film may be transformed as depicted in FIG. 3. Thus, the film within a small subregion 76 at the center of region 74 is substantially completely transformed to transparent copper oxide. A region of progressively diminishing partial transformation 78 immediately surrounds subregion 76. In a further subregion 80 adjacent the margin of region 74, the film is substantially untransformed.

After the heating pulse, control unit 68 commands the laser drive circuit 66 and laser 50 to emit a second measurement pulse, of substantially the same low energy as the first measurement pulse. The second measurement pulse impinges on the same localized region 74 of the film, and a portion of the light in the second measurement pulse passes to photodetector 54. Because the film within region 74 has been partially transformed from a reflective metallic film to a transparent, copper oxide film, less of the light in the second measurement pulse is reflected from region 74. Thus, the average reflectivity of the film within region 74 is lower during the second measurement pulse after heating, than during the first measuring pulse before heating, and less light reaches photodetector 54 during the second measurement pulse than during the first.

In response to the light impinging on photodetector 54 during the second measurement pulse, signal processing and amplification circuit 70 generates and transmits to control unit 68 a second signal $S_2$ having a value greater than the value of signal $S_1$ generated during the first measurement pulse. With a heating pulse of a predetermined power level and duration, and hence with a substantially fixed rise in the average temperature of the heated region 74 during the heating pulse, there is a substantially fixed relationship between the molecular concentration of oxygen at the film and the decrease in the average reflectivity of the film in region 74. The difference between the values of signals $S_2$ and $S_1$ varies directly with the decrease in reflectivity occasioned by the heating pulse. There is accordingly a fixed relationship between the difference in the values of signals $S_2$ and $S_1$ and the molecular concentration of oxygen at the surface during the heating pulse, and hence a fixed relationship between this difference and the proportion of oxygen in the gas passing through the apparatus.

This fixed relationship for a particular heating pulse power level and duration is depicted schematically by curve 82 in FIG. 5. Control unit 68 thus determines the difference in reflectivity of region 74 before and after the heating pulse by computing the difference D between the values of $S_2$ and $S_1$, and translates that difference into a percent oxygen value according to a translation schedule or formula corresponding to curve 82. That percentage oxygen value is displayed by output display unit 72.

For the next measurement, control unit 68 commands stepper drive 26 to rotate shaft 24, and hence body 32 by a small increment and then stop, so as to place a new, unexposed region of film 36 at the focus of lens 62 and hence within the active zone of the apparatus. The same sequence of a first measurement pulse, a heating pulse and a second measurement pulse, is repeated, and the oxygen concentration is determined again in the same manner. This cycle of operations is repeated for each succeeding measurement, stepper drive 26 being actuated to shift the body 32 stepwise on each cycle so as to place a fresh, unexposed region of the film within the active zone of the apparatus on each cycle. When stepper drive 26 has rotated shaft 24, and hence body 32 through a full circle, control unit 68 commands translation drive 42 to displace carriage 38 through a predetermined distance so as to shift the carriage radially with respect to body 32 and hence shift the active zone of the apparatus to a new portion of the film surface. When the entire film surface has been consumed in this manner, housing 20 is opened and the body 32 is removed, as by releasing bolt 30, and replaced by a new body.

As exemplified by curve 82 in FIG. 5, the relationship between the difference in reflectivity before and after the heating pulse and the oxygen concentration in the gas typically is substantially linear for a useful range of oxygen concentrations, indicated for curve 82 as the range between $C_{min}$ and $C_{max}$. Below $C_{min}$, the reflectivity of the illuminated region is diminished by only a very small amount by the reaction occurring during the heating pulse. At $C_{max}$, substantially all of the film within the entire illuminated region is transformed from metallic copper to transparent copper oxide. Thus, as indicated in FIG. 4, each localized region 74 is fully saturated; the fully transparent subregion 76' occupies substantially the entire localized region 74. Increased oxygen concentration, above $C_{max}$, cannot provide any appreciable further decrease in reflectivity. The useful range of the apparatus may be shifted by changing the energy of the heating pulse. Thus, curve 84 in FIG. 5 represents the relationship between difference in reflectivity before and after the heating pulse and oxygen for a heating pulse of lower power level and/or shorter duration, and hence lower energy, than the heating pulse which provides curve 82. The useful range for the heating pulse of curve 84 encompasses a higher oxygen concentrations than that of curve 82. Curve 86 represents the same relationship between difference in reflectivity before and after the heating pulse and oxygen concentration for a heating pulse of higher energy than the heating pulse of curve 82; the higher-energy heating pulse has a useful range encompassing lower oxygen concentrations.

Preferably, control unit 68, laser drive circuit 66, and laser 50 are configured to provide heating pulses with any of several preselected energy values. Thus, the apparatus can operate according to any of several different relationships between change in reflectivity and oxygen concentration, such as curves 82, 84 and 86, encompassing different useful ranges. Control unit 68 may be provided with a predetermined translation schedule or formula for each preselected heating pulse energy value. The control unit may be arranged to select and employ on each cycle the translation scheme corresponding to the heating pulse energy value employed on that cycle, so as to derive the correct value of oxygen concentration from the difference in reflectivity determined during the measurement pulses. Control unit 68 may also be arranged to vary the energy of the heating pulse employed on each cycle depending on the results obtained on one or more preceding cycles. Thus, where the difference in reflectivity before and after heating on one cycle exceeds a predetermined maximum, and hence indicates that the oxygen concentration is at or above the upper end of the useful range for the heating pulse energy employed on that cycle, control unit 68 may automatically select a lower heating pulse energy for the next cycle. Likewise, if the difference in reflectivity before and after heating on one cycle is less than a predetermined minimum, indicating that the oxygen concentration is at or below the lower end of the useful range for the heating pulse energy employed on that cycle, the control unit may automatically select a higher heating pulse energy for the next cycle. Feedback control of heating pulse energy may be based solely upon the value of reflectivity after heating, rather than upon the difference in reflectivity before and after heating. Thus, if the reflectivity of the localized region heated on one cycle corresponds to the reflectivity of a fully-transformed or saturated region, the control means may select a lower heating pulse energy for the next cycle.

In the embodiment described above, the change in reflectivity for each localized region of the film is determined by comparing measured values of reflectivity for that region before and after the heating pulse. This arrangement is preferred inasmuch as it compensates for differences in reflectivity prior to heating between various regions of the film, and also compensates for drift or changes in calibration of the elements used to measure reflectivity, such as the photodetector 54 and signal processing and amplification circuit 70. However, the measurement of reflectivity before heating can be omitted, in which case the change in reflectivity during the heating step can be determined by comparing the measured reflectivity of each region after heating with a standard value representing the average reflectivity of the film before heating. Thus, in a variant of the embodiment described above, the first measuring pulse can be omitted and the control unit can be arranged simply to translate the signal from photodetector 54 and signal processing and amplification circuit 70 responsive to the second or postheating measurement pulse into oxygen concentration values. In a further variant, the signal processing and amplification circuit 70 may be connected to an ordinary voltmeter, and the voltmeter may be adjusted to read zero at the signal voltage level corresponding to the average reflectivity of the film before heating. Thus, when the voltmeter receives a signal representing the reflectivity of the film after heating, the voltmeter will display a value representing the difference between reflectivity after heating and reflectivity before heating.

The radiant energy utilized to measure the reflectivity of the body surface need not be separate from the radiant energy used for heating. Thus, the reflectivity of the film may be monitored by monitoring the light reflected by the film during the heating pulse itself so as to utilize the heating radiant energy for reflectivity measurement as well. In this variant, photodetector 54, signal processing and amplification circuit 70 and control unit 68 may be arranged to capture a first signal value representing the amount of light reflected from the film during the beginning of a heating pulse and to capture a second signal representative of the amount of light reflected at the end of the heating pulse, and to compare those signals so as to determine the change in reflectivity of the film. In a further variant of this approach, the control unit 68 may be arranged to capture only a single signal representative of the amount of light reflected from the film during the last portion of the heating pulse, and hence representative of the reflectivity after heating, and to translate that single measurement into percent oxygen concentration based on a standard value for reflectivity before heating.

The oxygen concentration may also be determined from the rate of change in reflectivity during the reaction. Thus, photodetector 54, signal processing and amplification circuit 70 and control unit 68 may be arranged to capture a series of signal values representing the reflectivity of the film at a series of predetermined times during each heating pulse. The signal for each such time is compared to the signal for the next preceding time. In effect, this arrangement determines the degree to which reflectivity is reduced by the reaction during each of several parts of the heating pulse. As the interval between reflectivity measurements is known, the change in reflectivity between successive reflectivity measurements can be translated into a rate of change per unit time. Each such rate can be translated into an oxygen concentration value. Preferably, in such an arrangement, the control unit would be arranged to select the highest rates of change in reflectivity for translation into oxygen concentration values. The highest rates would be attained during the middle of each heating pulse, after the localized region being heated has attained a temperature sufficient to initiate oxidation but before the film in such region has been fully oxidized. In a further variant of this approach, the heating pulse power level and duration are selected so that during the complete heating pulse, the entire localized region is substantially transformed to copper oxide. Photodetector 54, signal processing and amplification circuit 70 and control unit 68 are arranged to continuously monitor the amount of light reflected from the film, and hence the reflectivity of the film during the heating pulse. The interval from the time the reflectivity begins to decline to the time the reflectivity stabilizes at a low value representative of substantially complete oxidation is determined. This interval is inversely proportional to the rate of oxidation during the heating step and hence is a measure of the oxygen concentration in the gas.

In the embodiment described above, the change in reflectivity of each localized region is determined immediately, before the next localized region is heated, so as to provide the oxygen concentration values in "real time," i.e., to report each oxygen concentration value before the next measurement is taken. However, as the change in reflectivity occasioned by oxidation of the film is permanent, each partially oxidized localized region of the film forms a permanent record of the oxygen concentration in the gas at the time of the heating pulse employed to heat that particular region. Thus, a series of oxygen concentrations measured at one time can be displayed again at a later time by subjecting the series of localized regions used for the measurement to measuring pulses, without further heating pulses. A series of localized regions may be subjected to heating pulses, without measuring pulses, so as to record the oxygen concentration without measuring it at the time of recordation. These localized regions can be subjected to measuring pulses at a later time to measure and display the recorded oxygen concentrations. In this variant, the heating pulses may be applied by recording apparatus identical to the measurement apparatus illustrated in FIG. 1 but omitting the photodetector 54 and the elements associated therewith. The body 32 can then be transferred to an apparatus as illustrated in FIG. 1 for playback of the recorded gas concentrations. For use in such a playback mode, the control unit 68 is arranged to operate laser drive circuit 66 and laser 50 only in the measurement mode, so as to emit only a single low power measurement pulse for each localized region of the film surface and to interpret the signal by the photodetector during each measurement pulse as a signal representative of the post-heating reflectivity of the film.

As will be readily appreciated, the particular optical and mechanical elements utilized in the apparatus of FIG. 1 are merely exemplary of the numerous different optical and mechanical elements which may be employed to direct radiant energy onto a series of localized regions of a body surface and to monitor the optical properties of each such localized region. Merely by way of example, numerous different moving mirror and/or moving prism arrangements may be used to selectively direct radiant energy onto various regions of a stationary body surface and hence to displace the active zone or focus of the radiant energy relative to the body surface. The relative movement of the surface and the active zone or focus of the radiant energy may be continuous rather than stepwise. Thus, a continuous heating beam from a continuous wave heating laser may be directed into a defined active zone and the recording medium or body may be moved continuously so that various regions of the body surface pass through the heating beam. In such an arrangement, the duration of exposure of each region to the heating beam is determined by the width of the heating beam and the speed of movement of the surface. In a further embodiment of the present invention, the molecular concentration of oxygen may be recorded and/or measured simultaneously at multiple locations. Thus, a plurality of heating pulses may be applied simultaneously to a plurality of regions remote from one another on the body surface, and the change in reflectivity of each such region may be evaluated as described above. This arrangement may be employed, for example, to study gas flow and mixing patterns in industrial or scientific apparatus. Thus, a body or recording medium may be fixedly mounted within a duct or flow channel, so that the film-bearing body surface extends through the duct, and plural regions of the film may be heated to record the oxygen concentrations at plural locations within the duct. In a further variant, the duct wall itself can serve as the body or recording medium.

The use of a thin film of reactive, metal-containing material on the surface of body 32 facilitates rapid heating of the film. As the thermal conductivity of the metal-containing film is proportional to its thickness, such conduction losses can be minimized by minimizing the thickness of the film. Accordingly, the metal-containing film should be less than 2,000 Angstroms thick, and thinner films, less than about 1,000 Angstroms thick are more preferred. The lower limit of film thickness is set principally by practical difficulties encountered in preparation of very thin, defect-free films. It is difficult to form coherent, defect-free copper-containing films less than about 400 Angstroms thick by conventional techniques. Accordingly, the film thickness range from about 400 to about 800 Angstroms is particularly preferred, and the range from about 600 to about 800 Angstroms is most preferred for copper-containing films.

Copper-containing films of the desired thickness may be applied to substrates by radio frequency sputtering techniques. Preferably, the atmosphere employed during sputtering consists essentially of an inert gas such as argon and a minor amount, such as approximately 1 percent by volume of a gas, such as oxygen or nitrogen reactive with the copper under sputtering conditions. The reactive gas reacts with the metallic copper to form a dopant such as copper oxide or copper nitride which is incorporated in the film. The dopant increases the absorptivity of the film and hence facilitates heating of the film by the radiant energy. Preferably, the film has an absorptivity of between about 5% and about 50% before heating. Copper nitride, as formed by sputtering in a nitrogen-containing atmosphere, is a particularly preferred dopant, as the nitride stabilizes the film against oxidation during room temperature storage.

Tin, silver and nickel can also be used in films for oxygen determination. Preferably, such films include one or more metals selected from the group consisting of copper, tin, silver or nickel. Indium or, preferably, antimony can be used in admixture with those metals, particularly with tin. One particularly useful film for oxygen determination includes 90% tin and 10% antimony, with tin and antimony nitride dopants. Tin and antimony films can be formed in substantially the same way as copper films; the same thickness ranges are preferred.

Regardless of the particular metal employed in the film, the application technique should be controlled carefully to provide good adhesion between the film and substrate. Poor film adhesion can result in separation of the film from the substrate upon heating, which in turn can produce spurious changes in reflectivity and hence inaccurate readings.

The substrate 34 underlying the film in the recording medium or body 32 preferably has thermal diffusivity less than about $10^{-2}$ cm$^2$/sec so as to limit heat loss from the film to the body. Substrate materials with still lower thermal diffusivity are more preferred. Preferably, the substrate is substantially nonreflective of the radiant energy utilized in the reflectivity measurements. The surface of the substrate underlying the film should be smooth. Nonmetallic materials such as glass and polymeric materials are preferred, and float glass is particularly preferred as a substrate.

The localized region heated by each heating pulse preferably is as small as possible. Thus, the optical elements of the apparatus are arranged to focus the radiant energy employed in each heating pulse to a narrow beam at the film surface. The lower limit for localized region size is determined principally by considerations of repeatability and controllability. Thus, as the size of each region decreases, microscopic defects in the film and minor deviations in the optical system become more significant. Each localized region preferably encompasses less than about $1 \times 10^{-4}$ cm$^2$ and more preferably between about $3 \times 10^{-5}$ cm$^2$ and about $7 \times 10^{-8}$ cm$^2$ of film surface area. Thus, where the localized regions are circular, they are preferably between about 60 microns and about 3 microns in diameter. Vast numbers of the preferred, small localized regions can be accommodated on a body or recording medium of reasonable size. For example, about $3 \times 10^8$ separate localized regions, each about 5 microns in diameter can be accommodated on a circular recording surface about 12.5 cm in diameter where 50% of the surface area is filled by the localized regions. Stated another way, such a disk provides enough recording surface to record one measurement per second, 24 hours a day, for nine years.

As set forth above, the required heating pulse energy varies with the film temperatures to be attained during the heating step, which in turn depends upon the desired useful range of oxygen concentrations. The required heating pulse energy also depends upon the thermal conductivity and diffusivity of the film and the substrate, the radiant energy absorptivity of the film, and the initial temperature of the film. Most significantly, however, the required heating pulse energy also varies directly with area of the localized region to be heated. Accordingly, minimizing the size of the localized region heated on each heating pulse minimizes the required heating pulse energy and hence minimizes the required heating pulse power and duration. Stated another way, for a given heating pulse power level, small localized regions permit brief heating pulses and hence permit repetition of the heating pulses at high frequencies or cycle rates to monitor rapidly-changing gas compositions.

With a typical metal-containing film, localized regions about 60 microns in diameter and about $2.8 \times 10^{-5}$ cm$^2$ area can be heated satisfactorily with 450 milliwatts of radiant energy in less than 500 milliseconds and typically in about 10 to about 200 milliseconds. Regions about 5 microns in diameter and about $2 \times 10^{-7}$ cm$^2$ in area can be heated in about 1 millisecond to about 10 milliseconds using only about 5 to 40 milliwatts heating pulse power. Power levels in the 5 to 40 milliwatt range can be provided by readily available, economical and simple diode lasers.

As pointed out above, the degree or rate of oxidation, and hence the degree or rate of change in reflectivity within each localized region of the film depends upon the molecular concentration of oxygen at the film surface. In the method described above, the gas pressure is substantially constant, so that the molecular concentration depends only on the proportion of oxygen in the gas. Thus, the change in reflectivity is translated into percent oxygen in the gas. Conversely, for a gas of fixed oxygen content, the molecular concentration depends solely on the total absolute pressure of the gas. Accordingly, with a gas of fixed oxygen content, the same methods as described above can be applied to measure or record the gas pressure. Merely by way of example, the pressure prevailing at many different locations on the surface of an aerodynamic model can be recorded on the surface of the model itself by directing heating pulses onto the model surface.

In the embodiments described above, the reaction of the gas at the surface of the body involves oxidation of the metallic film on the body surface by oxygen present in the gas. Other reactions involving other constituents in the gas may also be employed, to detect either the total pressure of the gas or the proportion of such other constituents in the gas. Thus, the molecular concentration of enflurane ($CFClHCF_2OCF_2H$) may be detected by contacting a gas containing enflurane as a constituent with a body having an aluminum surface and momentarily heating the aluminum surface. Although the present invention is not limited by any theory of operation, it is believed that the heated aluminum either reduces the enflurane or catalyzes its decomposition. Regardless of the actual reaction mechanism, the aluminum/enflurane reaction produces a dark, carbonaceous deposit on the body surface, thus reducing the reflectivity of the body surface. A recording medium or body for use in detection of enflurane according to this embodiment of the present invention may incorporate an aluminum film or a substrate as described above. Desirably, aluminum films utilized for this purpose contain a dopant of aluminum oxide or aluminum nitride. Aluminum-containing films may be formed on glass substrates by a radio frequency sputtering process substantially the same as utilized to deposit the other films described above. With aluminum-containing films, as with the other films referred to above, films less than 2,000, and preferably less 1,000 Angstroms thick, provide rapid response and hence are preferred. As high-quality aluminum-containing films as thin as 100 Angstroms can be formed by conventional techniques, aluminum-containing films between 100 and 500 Angstroms thick are particularly preferred, and aluminum-containing films between 200 and 400 Angstroms thick are most preferred. In other respects, the process and apparatus utilized for measurements of enflurane concentrations are substantially the same as those described above with reference to oxygen measurement. Thus, the reaction with enflurane produces a change in the reflectivity of the film, and the degree or rate of alteration in reflectivity during the heating step is monitored to provide a measure of the molecular concentration of enflurane at the body surface. Typically, enflurane containing gases are employed in medical applications as anesthetic mixtures, at approximately one atmosphere total absolute pressure. Under those conditions, the change in reflectivity of the aluminum film depends solely on the proportion of enflurane in the gas mixture, and is substantially unaffected by the presence or concentration of nitrous oxide, carbon dioxide, carbon monoxide and oxygen.

Other halogenated organic compounds will react in similar fashion with an aluminum containing body upon heating. Thus, the molecular concentration of such other halogenated organic compounds can be measured by the same techniques as employed with enflurane. The same aluminum film technique used with enflurane can also be employed with isoflurane ($CF_3CClHOCF_2H$) and halothane ($CF_3CHBrCl$), two other common anesthetic agents. However, isoflurane will react with the aluminum surface at a lower temperature than enflurane, and halothane will react with the aluminum surface at still lower temperatures. Thus, the heating pulse energies required to produce the decrease in reflectivity employed in molecular concentration measurements are lower for isoflurane than for enflurane, and are still lower for halothane. Accordingly, lower pulse energies are employed in molecular concentration measurements of halothane and isoflurane than are employed with enflurane.

Stated another way, for each of these constituents at a given molecular concentration, there is a particular relationship between heating pulse energy and the degree of darkening or loss of reflectivity, and these relationships are different for the three different constituents. In a method according to a further aspect of the invention, these differences can be employed to discriminate between the three different anesthetic agents and hence to identify an anesthetic agent present as a constituent in a gas, such as a breathing mixture supplied to a patient. The relationships between heating pulse energy and change in reflectivity ($\Delta R$) upon heating for the three anesthetic agents, each at a given molecular concentration typically encountered in anesthetic practice, are depicted schematically in FIG. 6. Solid line curve 90 depicts the relationship for enflurane, whereas broken line curve 92 indicates the relationship for isoflurane at the same molecular concentration and dashed line curve 94 depicts the corresponding relationship for halothane. For each of the three agents, the relationship between heating pulse energy and change in reflectivity includes an upwardly sloping meaningful range corresponding to progressively increasing carbonaceous deposit formation by the reduction and/or decomposition reaction. For pulse energies within the meaningful range of each curve, greater pulse energies produce a greater reaction of the agent at the aluminum surface and hence darken the aluminum surface to a greater degree, resulting in a larger change or decrease of reflectivity during the heating step. The upslope or meaningful range for enflurane is encountered at far higher pulse energies than the meaningful range for isoflurane or for halothane.

In one identification method according to this aspect of the invention, a gas containing an anesthetic agent is passed through an apparatus as illustrated in FIG. 1 but having an aluminum-containing film in place of copper-containing film 36. Control unit 68 commands laser drive circuit 66 and hence laser 50 to emit a measurement pulse, a heating pulse of known energy $E_1$ and then another measurement pulse. The difference in reflectivity of the film before and after the heating pulse is determined in the same way as described above with reference to molecular concentration measurements. The measured degree of change in reflectivity with the known heating pulse energy provide information as to the relationship between extent of heating and degree of change. That information can be compared to corresponding information for a gas containing a known constituent. If the change in reflectivity produced by pulse energy $E_1$ is $\Delta R_1$, then the anesthetic agent is identified as enflurane.

As seen most clearly with respect to curves 92 and 94, each curve also includes a scatter region at pulse energies higher than those associated with the meaningful upslope region At pulse energies in the scatter region of each curve, spurious decreases in reflectivity occur with increasing pulse energy. It is believed that these decreases in reflectivity are associated with a phenomenon referred to as "lensing." If the pulse energy is high enough that a dark deposit forms during the beginning of the pulse, then the remainder of the pulse is effectively absorbed by the deposit leading to uncontrolled heating, decomposition of the deposit and possibly pitting of the substrate itself. The pitted substrate tends to reflect light during the subsequent measurement. Regardless of the actual mechanism involved, pulse energies far higher than those required to complete the deposit formation process can give spurious low values for the change in reflectivity upon heating. These spurious values can cause ambiguity in the agent identification. For example, if the apparatus applies a heating pulse of energy $E_2$, a signal or change in reflectivity equal to Δ R₂ could be produced either by enflurane (in the meaningful region of curve 90) or by halothane or isoflurane in the scatter region. To eliminate any such ambiguity, the constituent identification method may include at least two determinations of change in reflectivity for different localized regions using different heating pulse energies. Thus, control unit 68 may be programmed to apply different heating pulse energies to different localized regions, correlate the change in reflectivity observed for each localized region with the heating pulse energy applied thereto and determine whether the change in reflectivity increases with increasing heating pulse energy so as to identify the upslope region. Preferably, only those determinations within the meaningful range are used in the comparison to identify the gas. The control unit may also be programmed to adjust the heating pulse energy applied to each localized region during the agent identification operation in response to the results of previous determinations. For example, if heating pulses of energies $E_2$ and $E_1$ both yield a signal or change in reflectivity Δ $R_2$, then the agent present cannot be enflurane. The control unit may respond to such results by applying pulses of lower energies $E_3$ and $E_4$ on the next cycles to test for the presence of isoflurane, and, if those are likewise unsuccessful, by applying still lower energy pulses on succeeding cycles to check for the presence of halothane, until a positive agent identification is established.

Ordinarily, the exact molecular concentration of the agent is not known in advance. As pointed out above, the response or change in reflectivity observed with a given agent and a given heating pulse energy varies with the molecular concentration. Thus, the relationship between heating pulse energy and change in reflectivity for a given agent at one molecular concentration will differ from the corresponding relationship for the same agent at another molecular concentration. For the molecular concentrations of anesthetic agents encountered in operation of ordinary anesthesia apparatus, however, these differences are small in comparison to the differences between the pulse energy/reflectivity change relationships for different agents, and hence do not interfere with the agent identification method.

Figure 6:
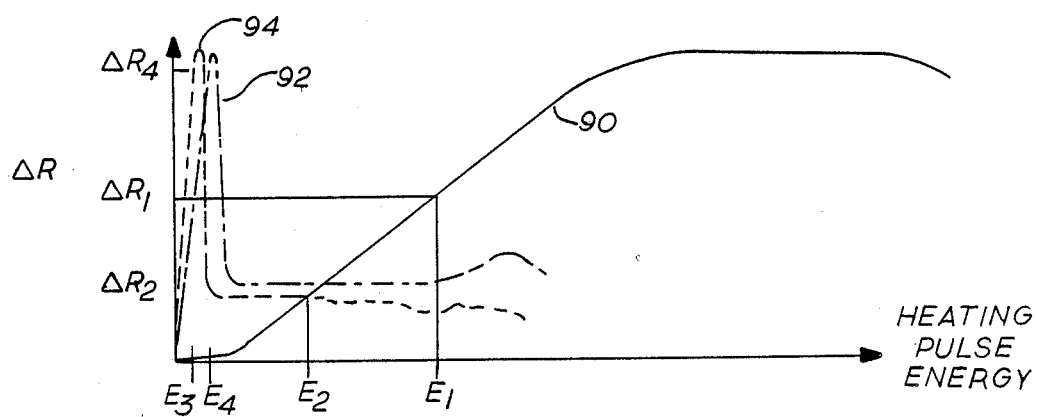
Figure 7:
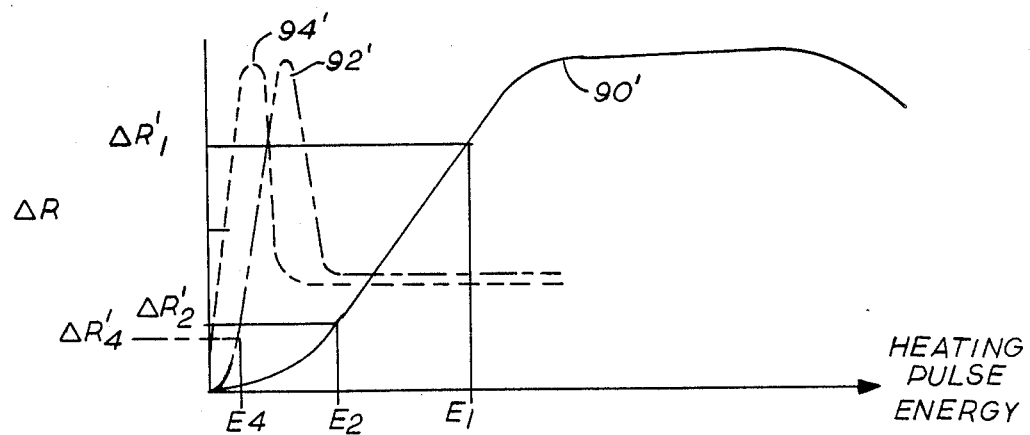

FIG. 7 schematically depicts the effects of the various agent concentrations which may occur in practice. Thus, curve 90' represents the relationship between heating pulse energy and change in reflectivity for a higher concentration of enflurane than that represented by curve 90 (FIG. 6). The meaningful or upslope range of curve 90' is steeper than that of curve 90. At energy $E_1$ the signal or change in reflectivity at the higher molecular concentration is $R_1'$ (FIG. 7) rather than $R_1$ (FIG. 6). Conversely, curves 92' and 94' indicate the pulse energy/reflectivity change relationships for lower concentrations of isoflurane and enflurane than those indicated by curves 92 and 94 (FIG. 6), respectively. Although the meaningful ranges for isoflurane and enflurane at the lower concentrations (FIG. 7) extend to somewhat higher pulse energies, there still is no substantial overlap between the meaningful ranges for these agents and the meaningful range for enflurane. Thus, if it is known that a gas contains one of the three anesthetic agents in a molecular concentration somewhere in the range of concentrations produced by common anesthetic equipment, and it is known that a heating pulse energy $E_1$ lies somewhere in the meaningful range for the agent in the gas, then the agent in the gas is positively identified as enflurane.

Once the agent in the gas has been identified, its molecular concentration can be determined as described above. Thus, control unit 68 may be programmed to compare the relationships between heating pulse energy and signal or change in reflectivity so as to identify the agent as described above and then select an appropriate heating pulse energy for measurement of the concentration of that agent and also select an appropriate translation schedule or formula for converting observed changes in reflectivity during concentration measurements into concentrations of the identified agent. As will be appreciated, the agent identification procedure can be completed quickly; the time required for agent identification is merely the time required for application of the appropriate heating and measurement pulses to a few localized regions of the film surface.

In the agent identification methods described above, the heating pulse energy is adjusted until a reaction occurs and the reflectivity of the surface is reduced, to a substantial degree, by the reaction. The relationship between heating pulse energy and change in reflectivity is determined from the pulse energy required to produce this change in reflectivity, so as to positively identify the agent present. In some cases, however, it is not necessary to adjust the heating pulse energy until the reaction occurs. Thus, the presence of an incorrect anesthetic agent can be detected by establishing a "negative identification" of the anesthetic agent present in a breathing gas, i.e., by establishing that the agent in the mixture is not the intended or correct agent. A single localized region may be heated by a single pulse of the appropriate energy to produce a reaction, and hence a change in reflectivity where the correct agent is present. If the predicted change does not occur, then the correct agent is not present. For example, a heating pulse of energy $E_4$ (FIGS. 6 and 7) may be applied to test for the presence of isoflurane. As evident from FIGS. 6 and 7, such a heating pulse should produce a change in reflectivity somewhere between Δ$R_4'$ (FIG. 7) for a low concentration of isoflurane and Δ$R_4$ (FIG. 6) for a high concentration If a change in reflectivity within this range does not occur upon application of a heating pulse of energy $E_4$, then the agent present in the gas is not isoflurane. Thus, control unit 68 may be programmed with the identity of the intended or agent and may be arranged to actuate an alarm if the intended agent is not present.

Such a warning provides an important safety measure in anesthesia administration, even without precise identification of the agent actually present. Typical anesthesia administration systems include an anesthetic agent reservoir and a vaporizer for mixing the anesthetic agent from the reservoir with the other components of the breathing gas mixture. If the incorrect agent is placed in the reservoir, the incorrect agent can be administered to the patient with deleterious results. Such misfilling can be detected by identification methods according to the present invention. Moreover, such detection is accomplished by the same apparatus as employed to and measure the concentration of the agent in the gas stream supplied to the patient. The reliability and utility of the agent identification method can be increased by operating the anesthesia administration system during the identification process under predetermined conditions which will provide a predetermined molecular concentration of the correct agent if the correct agent is present in the agent reservoir. For example, the vaporizer may be set to provide the relatively low concentration of isoflurane corresponding to curve 92' (FIG. 7). If the observed change in reflectivity with a heating pulse of energy $E_4$ from the expected change $R_4'$ by any significant amount, then either the incorrect agent is present or the vaporizer is defective.

Similar methods can be employed to identify gas constituents other than anesthetic agents. For example, the halogenated lower hydrocarbons commonly employed as refrigerants react with aluminum surfaces upon heating in much the same way as do the anesthetic agents. The different refrigerants in this series have different reactivities. Thus, the relationship between change in reflectivity and heating pulse energy is different for each of the different refrigerants in the series. Thus, methods according to this aspect of the present invention can be used to determine the identity of a refrigerant in this series or to detect the absence of the correct refrigerant in a refrigeration system.

Films other than aluminum can be used in measurement and identification methods for organic constituents. Thus, the group VIII metals, notably palladium and ruthenium produce darkening effects similar to those produced by aluminum. Bodies having films containing palladium or ruthenium can be used in substantially the same fashion as bodies having aluminum-containing films. Typically, ruthenium is employed in the form of ruthenium dioxide.

Reactions involving constituents other than those mentioned above may also be employed in measurement and identification methods and apparatus according to the present invention. The material of the body surface may participate in the reaction either as a catalyst or as a reactant. In a further variant, the gas constituent may react at the body surface in a reaction which does not involve the body surface material either as a catalyst or as a reactant. Thus the reaction of the gas at the body surface may entail simple decomposition or transformation of an organic or other complex gas constituent molecule upon exposure to the heated body surface to form a solid deposit on the body surface surface, thereby altering a property of the surface. Desirably, the reaction is a "first order" reaction with respect to the gas constituent of interest, so that the rate of reaction is proportional to the first power of the molecular concentration.

In each of the embodiments described above, the reflectivity of the body surface is altered by the reaction of the gas at the body surface and the degree or rate of such alteration is determined. However, surface properties other than reflectivity may be altered by the reaction and may be determined to provide the measurement of molecular concentration or the identification information. In the arrangement employing a copper or tin containing film, the reaction converts the reflective copper or tin to substantially transparent copper oxide or tin oxide. Thus, the transmissivity of the film rather than its reflectivity may be measured. Manifestly, the substrate should be transparent to permit transmissivity measurement. Properties other than optical properties may be altered by the reaction and monitored. Merely by way of example, the electrical conductivity of the body surface may be permanently altered by the reaction of the gas at the body surface during the heating step.

The radiant energy employed in heating the body surface most preferably is light. As utilized in the present disclosure the term "light" includes infrared and ultraviolet radiation, as well as visible light, and hence encompasses the region of the electromagnetic spectrum from about 150 to about 12,000 nm wavelength. Light is preferred as the radiant energy for heating the body surface because light can be readily focused on a small localized region of the surface. However, other forms of radiant energy, such as microwave radiation, electron beam radiation, x-ray radiation and the like may also be employed. The surface of the body also can be heated momentarily by means which do not employ radiant energy. For example, an electrical current can be applied in a metallic film at the body surface to thereby momentarily heat the film. Also, the body surfaces can be heated momentarily by momentarily heating the entire body. However, such arrangements necessarily would entail a markedly slower response time and hence are less preferred.

Figure 8:
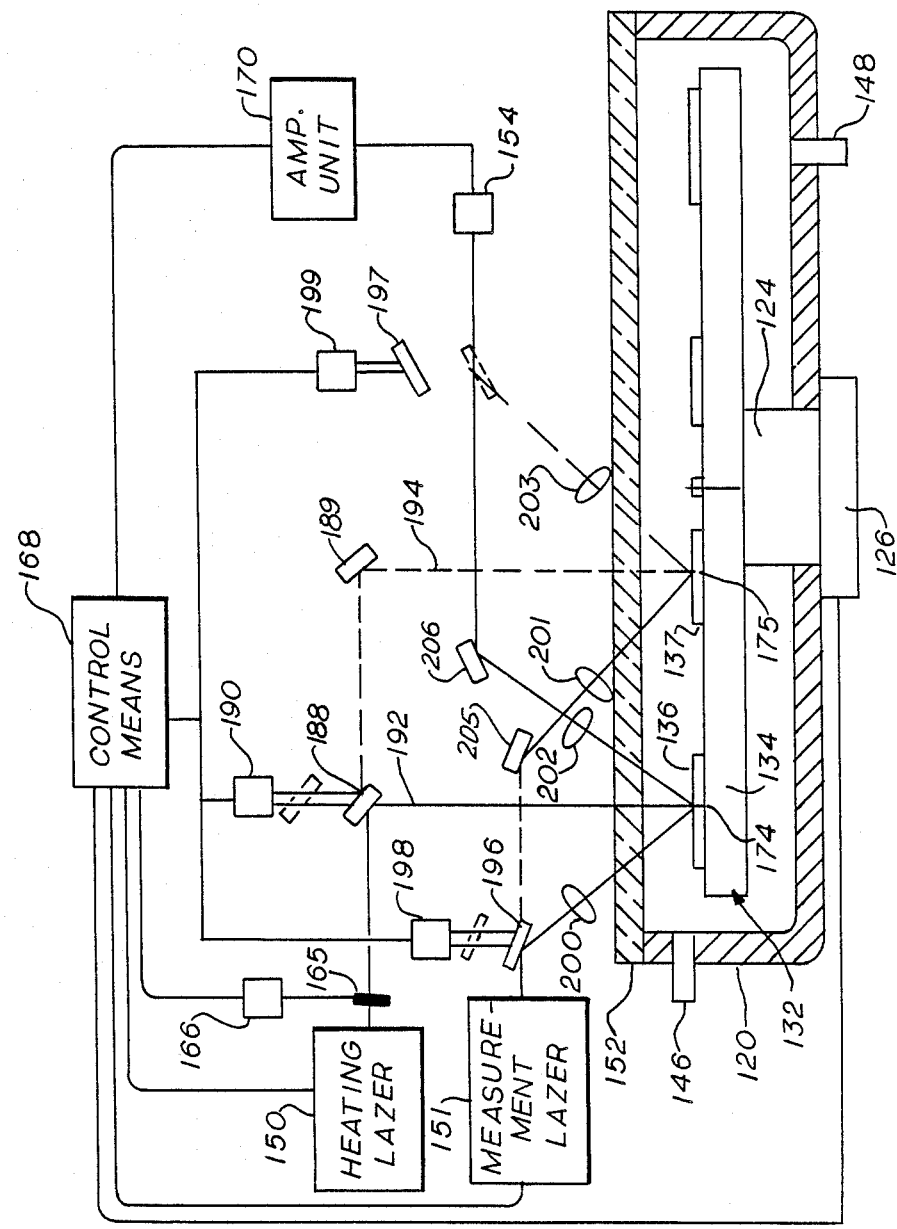
FIG. 8 is a schematic, partially sectional view depicting apparatus in accordance with another embodiment of the present invention.

The apparatus illustrated in FIG. 8 is generally similar to the apparatus illustrated in FIG. 1. The apparatus includes a housing 120 having a transparent wall or window 152. A shaft 124 and stepper motor drive 126 are mounted to housing 120. The apparatus of FIG. 8 includes a separate heating laser 150 and measurement laser 151 rather than the single laser used in the embodiment of FIG. 1. Heating laser 150 is a continuously operating yittrium aluminum garnet, or YAG, laser, whereas measurement laser 151 is a helium neon pulse laser. Heating laser 150 is provided with a mechanical shutter 165 and shutter actuator 166, which in turn is linked to the control unit 168 of the apparatus to provide a heating pulse of the desired duration A mobile optical element or mirror 188 is linked to an actuator 190, which is also connected to the control means 168. Mobile optical element 188 may be interposed in the path of light issuing from heating laser 150 so as to direct such light along a first optical path 192 into a first active zone 174. When the mobile optical element 188 is not interposed, the light from laser 150 is directed by fixed mirror 189 along a second optical path 194, indicated in broken lines, into a second active zone 175. Additional mobile optical elements 196 and 197, are connected to actuators 198 and 199 respectively. Actuators 198 and 199 are linked to control unit 168. Thus, the control unit can operate actuators 198 and 199 to direct light from measurement laser 151 either into the first active zone 174 via mobile element 196 lens 200 or into the second active zone via fixed mirror 205 and lens 201, and to direct light reflected from the active zones either via lens 202 and fixed mirror 206 or via lens 203 and mobile element 197 to the photodetector 154.

The body or recording medium 132 employed with the apparatus of FIG. 8 includes a disklike glass substrate 134 and two separate films 136 and 137 in separate surface areas or zones on substrate 134. As illustrated, films 136 and 137 are disposed in the form of concentric rings on substrate 134. Film 136 is aligned with the first active zone 174 of the optical apparatus, whereas film 137 is aligned with the second active zone 175. The two films are of different compositions, and are sensitive to different constituents in a gas mixture. For example, film 136 may be a copper film, sensitive to oxygen in the gas, whereas film 137 may be an aluminum film, sensitive to enflurane. A gas may be passed through housing 120 via input port 146 and outlet port 148, so that the gas contacts both films 136 and 137. Heating radiant energy from heating laser 150 may be directed onto either film 136 or 137 by operation of actuator 190 and mobile optical element 188. The change in reflectivity of each localized region of each of films 136 and 137 may be determined by measurement laser 151, photodetector 154 and signal processing and amplification unit 170, in conjunction with actuator and optical element assemblies 196 and 198. Thus, the reflectivity of localized regions of each of films 136 and 137 may determined before and after heating, so as to determine the molecular concentrations of oxygen and enflurane respectively.

Lenses 200 and 201 are arranged to focus the light from measurement laser 151 to a slightly larger beam diameter than the light from heating laser 150 at the film surfaces. Thus, the area illuminated by each measurement pulse from laser 151 will extend slightly beyond the corresponding localized region heated by a pulse from laser 150. This arrangement assures that each measuring pulse will detect changes in reflectivity throughout the entire heated region despite minor changes in the alignment of the optical elements.

As will be readily appreciated, the recording medium may incorporate more than two different films, and multiple films may be applied to various areas of the body in many different arrangements. Various different optical elements, other than the mobile mirrors illustrated in FIG. 8, may be employed to selectively direct heating and measurement radiant energy onto any of the multiple films. A single laser may be employed to provide both the heating and measurement radiant energy in a multiple film arrangement as illustrated in FIG. 8. Conversely, separate heating and measurement lasers may be employed in a single-film arrangement as illustrated in FIG. 1.

As pointed out above, the present invention can be employed to provide a permanent record of gas composition or pressure. The gas reaction used in the present invention may also be used to encode additional information on the body or recording medium. Thus, the laser employed to apply the heating pulses may be adjusted to a relatively high pulse energy to assure that each heating pulse will result in substantially complete transformation of the corresponding localized region under the prevailing gas concentration. Such high-energy digitizing pulses are applied to encode binary information on the body surface; to encode a "1" in a particular localized region, that region is exposed to a high-energy digitizing pulse. To encode an "0" in a localized region, that region is left unexposed. The digitizing pulses are thus applied in a pattern corresponding to the digital information, to mark the surface in such pattern by reaction of the gas constituent at each exposed region. The control means used to control the heating laser can be linked to digital information processing or input means, such as a keyboard, for this purpose. Such digitally encoded information may be read back using the same photodetector and signal-processing unit as employed to measure reflectivity. As a series of measurement light pulses are applied to a series of localized regions bearing the encoded digital information, the photodetector and signal-processing unit will provide a series of high and low output pulses, which in turn can be processed by standard digital circuitry. The digital information encoding capability may be used to record information related to the molecular concentration record. For example, where the molecular concentration record relates to administration of anesthesia, the patient's name, date, and the like may be digitally encoded on the same recording medium to provide a permanent label for the recorded concentration data.

In a further variant, the measurement method can be reversed to detect variations in the composition and/or thickness of a film, such as a metallic film, on a substrate. Thus, a known gas constituent is applied to the film at a substantially constant molecular concentration and various localized regions of the film are under substantially the same conditions, as by exposure to heating radiant energy pulses of the same energy content. If the film is of uniform thickness and composition, a property of the film surface, such as reflectivity, will be altered to the same extent in each region by reaction of the gas constituent. Variations in film thickness will affect the thermal conductivity of the film and hence will affect the temperature achieved by the various localized regions and the extent of the reaction in each region. Also, differences in film composition will affect the extent of the reaction. Thus, non-uniformities in film composition and/or thickness can be detected by monitoring the altered surface property, such as reflectivity, in each localized region, and detecting differences in such altered property.

The following examples illustrate certain aspects of the present invention.

EXAMPLE I

A recording medium is made by sputtering copper onto a float glass microscope cover slip under about 4 microns total gas pressure in an atmosphere of about 99% argon and about 1% nitrogen. The film is about 700 angstroms thick and consists principally of free or metallic copper, with some copper nitride incorporated as a dopant.

The cover slips are contacted with a gas mixture by placing each cover slip into an enclosed chamber having a transparent window and passing the gas mixture through the chamber under approximately atmospheric pressure. Localized regions of the copper film on each cover slip are heated by directing a YAG laser beam (1.06 micron wavelength) onto the copper film. A mechanical shutter is employed for control of heating pulse duration. The YAG laser light used for heating is focused to a circular spot about 50–70 microns in diameter at the film surface. The reflectivity of each localized region of the film is measured, before and after heating, by directing 5 milliwatt measurement pulses from a helium neon laser (0.632 micron wavelength) onto each region and monitoring the reflected light with a photodiode.

The output of the photodiode is processed by a signal conditioning circuit to provide a DC output voltage inversely proportional to the reflectivity of the film. The signal conditioning circuit is adjusted to zero output voltage during that first measurement pulse for each region prior to heating. The output voltage obtained during the second or post-heating measurement pulse for each region thus indicates the decrease in reflectivity of the region during the heating step.

With YAG laser heating pulses of 450 milliwatts power and 66 milliseconds duration, the DC output voltage obtained during the second measurement pulse for each region varies substantially linearly with the percentage of oxygen in the gas for oxygen contents between about 20% and about 70%. Within this useful range, the output signal voltage Vo corresponds to the oxygen concentration according to the formula $V_o$ (millivolts) $= 1.16 \times O_2(\%)$. The output signal is reproducible upon repeated measurements under fixed oxygen concentration. This reproducibility is confirmed by microscopic examination of various regions of the film after exposure to the YAG laser light heating pulses. The appearance of the various regions heated at a fixed oxygen concentration does not vary detectably, even at 450× magnification.

EXAMPLE II

The experiment of Example I is repeated using a YAG laser heating pulse of about 470 milliwatts power and about 125 milliseconds duration. The output signal is substantially linear for oxygen concentration in the useful range of about 0% to about 30%. Within the 0–30% oxygen range, the output signal voltage Vo corresponds to the oxygen concentration according to the formula: Vo (millivolts)=$3.66 \times O_2$ (%). In other respects, the results are the same as achieved in Example I.

EXAMPLE III

Recording media are prepared by sputtering aluminum onto glass cover slips using an atmosphere consisting of 99.5% argon and 0.5% nitrogen under a pressure of about $4 \times 10^{-3}$ torr to provide an aluminum film about 300 Angstroms thick with a minor amount of aluminum nitride dopant. The aluminum coated cover slips are contacted with gas mixtures containing enflurane and exposed to helium neon laser measurement radiation and YAG laser heating radiation in substantially the same manner as employed in Examples I and II. Each YAG laser heating pulse has a power level of 500 milliwatts and a 500 millisecond duration. The output signal varies reproducibly with enflurane content for enflurane concentrations between about 0% and about 7% by volume.

What is claimed is:

1. A method of measuring the molecular concentration of a constituent in a gas comprising the steps of:
   (a) contacting the gas with a surface of a solid body;
   (b) momentarily heating said surface so that said constituent reacts at said surface to alter a property of said surface permanently; and
   (c) determining the degree or rate of alteration in said property produced by reaction of said constituent during said momentary heating step, said heating step including the step of momentarily applying heating radiant energy to said surface in a plurality of heating pulses to a plurality of different localized regions of said surface in temporal sequence, said determining step being performed separately for each of said localized regions to thereby provide a plurality of measurements of said molecular concentration, whereby each of said measurements is indicative of said molecular concentration at the time of one of said pulses.

2. A method as claimed in claim 1 wherein said property is an optical property.

3. A method as claimed in claim 1 wherein said gas is contacted with said solid at a predetermined total pressure, whereby the measured molecular concentration of said constituent is a measure of the proportion of said constituent in said gas.

4. A method as claimed in claim 1 wherein the proportion of said constituent in said gas is predetermined, whereby the measured molecular concentration of said constituent is a measure of the total pressure of said gas.

5. A method as claimed in claim 1, wherein said surface of said body includes a plurality of surface zones of different composition, said contacting step includes contacting said gas with each of said zones, said heating step includes heating separate localized regions in each of said zones, different constituents of said gas reacting at the surface in each of said zones, said determining step being performed separately with respect to each of said separate localized regions in each of said different zones so as to measure the respective molecular concentrations of each of said different constituents.

6. A method as claimed in claim 1 wherein said constituent is an anesthetic selected from the group consisting of enflurane, halothane and isoflurane, the anesthetic reacting to form a deposit on said surface during said heating step to thereby lower the reflectivity of said surface, said determining step including the step of measuring the reflectivity of said surface after said heating step.

7. A method as claimed in claim 1 wherein the determining step for each localized region is performed before the next heating pulse is applied to the next localized region, to thereby provide a series of measurements of said molecular concentration in real time.

8. A method as claimed in claim 7, further comprising the step of controlling the energy content of each of said heating pulses in response to the result of said determining step for a region heated by a prior heating pulse.

9. A method as claimed in claim 1 wherein each of said localized regions encompasses about $1 \times 10^{-4}$ cm$^2$ or less of said surface.

10. A method as claimed in claim 9 wherein each of said heating pulses is less than about 500 milliseconds in duration.

11. A method as claimed in claim 10 wherein said body includes a thermally insulating substrate and a metal-containing film less than about 2,000 Angstroms thick on said substrate at said surface.

12. A method as claimed in claim 1 wherein said body is oxidized at said surface by said constituent.

13. A method as claimed in claim 12 wherein said constituent is oxygen.

14. A method as claimed in claim 13 wherein said body includes at said surface at least one metal selected from the group consisting of tin, silver, nickel and copper.

15. A method as claimed in claim 1 wherein said constituent reacts at said surface to form a solid product and said solid product is deposited on said surface.

16. A method as claimed in claim 15 wherein said constituent is an organic compound and said body includes at said surface a catalyst promoting decomposition of said organic compound during said heating step.

17. A method of recording the molecular concentration of a constituent in a gas comprising the steps of:
   (a) contacting the gas with a surface of a solid body; and
   (b) momentarily heating said surface so that said constituent reacts at said surface to alter permanently a property of said surface, the degree of alteration being dependent upon said molecular concentration present at said surface during said momentary heating step, said step of momentarily heating said surface including the step of applying a plurality of pulses of heating radiant energy to a plurality of different localized regions of said surface, said pulses being applied in temporal sequence, whereby the degree of alteration of said property in each of said localized regions is representative of said molecular concentration at the time of one of said pulses.

18. A method as claimed in claim 1 or claim 17 further comprising the step of recording digitally-encoded information on said surface by applying digitizing pulses of radiant energy to further localized regions of said surface in a pattern corresponding to said information, while contacting said gas with said surface so that said constituent reacts at said surface to thereby alter said property of said surface, whereby said further localized regions are marked by said reaction.

19. A method as claimed in claim 17 wherein each of said localized regions encompasses about $1 \times 10^{-4}$ cm$^2$ or less of said surface.

20. A method as claimed in claim 19 wherein each of said pulses is less than about 500 milliseconds in duration.

21. A method as claimed in claim 20 wherein said body includes a thermally insulating substrate and a metal-containing film less than about 2,000 Angstroms thick on said substrate at said surface.

22. A method of measuring the molecular concentration of a constituent in a gas comprising the steps of:
(a) contacting the gas with a surface of a solid body;
(b) momentarily heating said surface so that said constituent reacts at said surface to alter a property of said surface; and
(c) determining the degree or rate of alteration in said property produced by reaction of said constituent during said momentary heating step,
said heating step including the step of momentarily applying heating radiant energy to said surface in a plurality of heating pulses to a plurality of different localized regions of said surface, said determining step being performed separately for each of said localized regions to thereby provide a plurality of measurements of said molecular concentration, the determining step for each localized region including the step of measuring the reflectivity or transmissivity of that localized region at or after the end of the heating pulse applied to such localized region.

23. A method as claimed in claim 22 wherein the determining step for each localized region also includes the step of measuring the reflectivity or transmissivity of that localized region at or before the beginning of the heating pulse applied to such localized region.

24. A method as claimed in claim 22 wherein each of said localized regions emcompasses about $1 \times 10^{-4}$ cm$^2$ or less of said surface, and each of said heating pulses is less than about 500 milliseconds in duration, and wherein said reflectivity or transmissivity of said surface in each said localized region is permanently altered by said reaction of said constituent at said surface.

25. A method of identifying an unknown constituent in a gas comprising the steps of:
(a) contacting the gas containing the unknown constituent with a surface of a solid body;
(b) momentarily heating said surface to a known extent during said contacting step;
(c) measuring the degree of alteration, if any, in a property of said surface caused by reaction of the unknown constituent at said surface during said heating step so as to provide information as to the relationship between extent of heating and degree of alteration in said surface property for the gas containing the unknown constituent; and
(d) comparing the information obtained in step (c) with corresponding information for at least one gas containing a known constituent, said heating step including the step of heating a localized region of said surface to an extent sufficient to permanently alter said property of said surface to a substantial degree by applying a pulse of heating radiant energy to said localized region, said comparing step including the step of comparing the extent of heating required to produce said substantial degree of alteration in said property of said surface with the extent of heating required to produce corresponding alteration with gases containing known possible constituents.

26. A method as claimed in claim 25 further comprising the steps of repeating said heating step so that a different localized region of said surface is heated on each repetition of said heating step, varying the extent of heating on each repetition so as to heat different localized regions to different extents, determining the degree of alteration in said property separately with respect to each of said localized regions, selecting at least two of said localized regions for which the determined degree of alteration varies directly with the extent of heating, and performing said comparing step with respect to at least one of said selected localized regions.

27. A method as claimed in claim 26 wherein said varying step includes the step of controlling the energy of each heating pulse in response to the result of said determining step for a region heated on a prior pulse.

28. A method as claimed in claim 25 wherein said unknown constituent is believed to be a given, correct constituent, said heating step includes the step of heating said surface to a predetermined extent sufficient to produce a substantial expected degree of alteration in said property if said correct constituent is present in said gas and said comparing step includes the step of comparing the degree of alteration actually produced with said expected degree of alteration.

29. A method as claimed in claim 28 further comprising the step of providing an alarm signal if said actual degree of alteration produced resulting from said heating step does not match said expected degree of alteration.

30. A method as claimed in claim 29 further comprising the step of supplying said gas by operating a gas supply system having a constituent reservoir under predetermined conditions which will produce a predetermined molecular concentration of said correct constituent in said gas if said correct constituent is present in said constituent reservoir.

31. A method as claimed in claim 29 wherein said body includes a material selected from the group consisting of aluminum, aluminum nitride, palladium and ruthenium dioxide on said surface.

32. Apparatus for recording the molecular concentration of a constituent in a gas comprising:
(a) means for retaining a solid body;
(b) means for contacting a gas containing a constituent with said body;
(c) means for momentarily heating a surface of said body so that said constituent reacts at said surface to permanently alter a property of said surface and so that the degree or rate of alteration in said property depends upon the molecular concentration of said constituent at said surface during said momentary heating, said heating means including heating pulse means for applying a series of momentary pulses of heating radiant energy to said surface, and directing each pulse of heating radiant energy to a different localized region of said surface.

33. Apparatus as claimed in claim 32 further comprising means for determining the degree or rate of a alteration of said property separately with respect to each of said localized regions to thereby measure said molecular concentration.

34. Apparatus as claimed in claim 33 wherein said determining means includes means for applying measurement radiant energy to each of said localized regions and detector means for measuring the amount of said measurement radiant energy reflected from or transmitted through each of said localized regions.

35. Apparatus as claimed in claim 34 wherein said means for applying measurement radiant energy is operative to direct measurement radiant energy onto each of said localized regions both before and after the region is heated by said heating means, said detector means being operative to detect the radiant energy reflected or transmitted by each localized region both before and after the region is heated.

36. Apparatus as claimed in claim 34 wherein said heating pulse means and said measurement radiant energy applying means include means for directing said heating radiant energy pulses and said measurement radiant energy into an active zone, and shift means for shifting said active zone and said body with respect to one another to thereby align different localized regions of said surface with said active zone in temporal sequence.

37. Apparatus as claimed in claim 36 wherein a single common laser serves both as part of said heating pulse means and as part of said measurement radiant energy applying means, the apparatus further comprising control means for operating said common laser in a high-power mode to provide said heating radiant energy pulses and in a low-power mode to provide said measurement radiant energy.

38. Apparatus as claimed in claim 36 wherein said shift means is operative to shift said body and said active zone stepwise, the apparatus also including control means for coordinating operation of said heating pulse means, said measurement radiant energy applying means and said shift means so that said body is stationary with respect to said active zone during each heating radiant energy pulse and during application of said measurement radiant energy.

39. Apparatus as claimed in claim 32 further comprising a body retained by said body retaining means, said body including a thermally nonconductive substrate and a metal-containing film on said substrate at said surface.

40. A medium for recording or determinng the molecular concentration of a constituent in a gas comprising a body having a surface which is substantially nonreactive with a first constituent in a gas at a first temperature, said surface being reactive with said first constituent upon heating to a second temperature higher than said first temperature so that a property of said surface will be permanently altered by reaction with said first constituent upon such heating, said medium further comprising means for engaging the body-retaining means of a gas constituent measurement and/or recording apparatus, said body including a substrate and a first film on said substrate at said surface, said substrate being substantially nonreactive with said constituent, said film being reactive with said constituent at said second temperature but substantially nonreactive with said constituent at said first temperature, the light absorptivity of said film being between about 5% and about 50%, said substrate having a thermal diffusivity of less than about $10^2 cm^2/sec$, said film including at least one metal and said film being less than about 2,000 Angstroms thick.

41. A medium as claimed in claim 40 wherein said substrate has a flat surface and said film is disposed on said flat surface of said substrate.

42. A medium as claimed in claim 40 wherein said film includes at least one metal selected from the group consisting of aluminum and the group VIII metals.

43. A medium as claimed in claim 42 wherein said film includes a dopant selected from the group consisting of the oxides and nitrides of aluminum and the group VIII metals.

44. A medium as claimed in claim 45 wherein said film includes aluminum and is between about 100 and about 500 Angstroms thick.

45. A medium as claimed in claim 40 wherein said substrate is glass.

46. A medium as claimed in claim 40 further comprising a second film on said substrate, said second film being of different composition than said first film, said second film being substantially nonreactive with said first constituent of said gas but reactive with a second constituent of said gas.

47. A medium as claimed in claim 46 wherein said first film includes at least one metal selected from the group consisting of tin, silver, nickel and copper, and said second film includes at least one metal selected from the group consisting of aluminum and the group VIII metals.

48. A medium as claimed in claim 40 wherein said film includes at least one metal selected from the group consisting of tin, silver, nickel and copper.

49. A medium as claimed in claim 48 wherein said film includes tin and also includes antimony or indium.

50. A medium as claimed in claim 48 wherein said film includes copper and is between about 400 and about 800 Angstroms thick.

51. A medium as claimed in claim 48 wherein said film includes a dopant selected from the group consisting of the oxides and nitrides of tin, silver, nickel and copper.

52. A medium as claimed in claim 51 wherein said dopant is a nitride.

53. A method of measuring the molecular concentration of an anesthetic in a gas comprising the steps of:
  (a) contacting a gas containing an anesthetic selected from the group consisting of enflurane, halothane and isoflurane with a surface of a solid body incorporating at said surface a metal selected from the group consisting of aluminum and the group VIII metals;
  (b) momentarily heating said surface so that the anesthetic reacts at the surface to form a deposit on the surface during the heating step to thereby lower the reflectivity of said surface; and
  (c) determining the degree or rate of alteration in the reflectivity of the surface produced by said momentary heating step.

54. A method as claimed in claim 53 wherein said body includes aluminum at said surface.

55. A method as claimed in claim 54 wherein said body includes aluminum nitride at said surface.

* * * * *